United States Patent [19]

Korpman

[11] Patent Number: 4,540,415
[45] Date of Patent: Sep. 10, 1985

[54] DISPOSABLE DIAPER WITH A REPOSITIONABLE TAPE TAB FASTENER

[75] Inventor: Ralf Korpman, Bridgewater, N.J.

[73] Assignee: Personal Products Company, Milltown, N.J.

[21] Appl. No.: 400,553

[22] Filed: Jul. 21, 1982

Related U.S. Application Data

[63] Continuation-in-part of Ser. No. 348,470, Feb. 12, 1982, abandoned.

[51] Int. Cl.³ .......................... A61L 15/06; C09J 7/02
[52] U.S. Cl. .................................... 604/390; 604/389; 427/208.4
[58] Field of Search ............... 604/358, 386, 389, 390, 604/370, 372; 427/208.4; 428/352

[56] References Cited

U.S. PATENT DOCUMENTS

| | | | |
|---|---|---|---|
| 2,649,858 | 8/1953 | Le Bolt | 604/389 |
| 3,797,495 | 3/1974 | Schmidt | 604/390 |
| 4,024,312 | 2/1977 | Korpman | 428/343 |
| 4,063,559 | 12/1977 | Tritsch | 604/390 |
| 4,080,348 | 3/1978 | Korpman | 260/27 BB |
| 4,136,699 | 1/1979 | Collins et al. | 604/390 |
| 4,163,077 | 7/1979 | Antonsen et al. | 428/355 |

OTHER PUBLICATIONS

"Comp. for Con. of Therm. Adh.", Koda et al., Chem. Abs., vol. 89, p. 57, 1978, 89:130695d.

Primary Examiner—Richard J. Apley
Assistant Examiner—Greg Beaucage
Attorney, Agent, or Firm—Martha A. Michaels

[57] ABSTRACT

A disposable diaper is provided which has a pressure-sensitive adhesive closure, a moisture-permeable facing sheet, and a polyethylene moisture-impermeable backing sheet. The pressure-sensitive adhesive closure has an adhesive composition that permits reopening the diaper numerous times without substantial damage to the polyethylene backing sheet or to the adhesive closure.

5 Claims, 8 Drawing Figures

DISPOSABLE DIAPER WITH A REPOSITIONABLE TAPE TAB FASTENER

This application is a continuation-in-part of copending application Ser. No. 348,470, filed Feb. 12, 1982, now abandoned.

BACKGROUND OF THE INVENTION

This invention relates to disposable diapers having a pressure-sensitive adhesive closure. More particularly, the invention relates to disposable diapers having a reopenable and resealable pressure-sensitive adhesive closure.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al and U.S. Pat. No. Reissue 26,151 to Duncan et al.

As may be seen from the above-cited patents, it is desirable to obviate the problems that are inherent in closure systems which utilize extraneous fasteners such as safety pins, snaps and zippers. To this end, adhesive closure systems have presented acceptable solutions, however adhesive systems known thus far, once applied to the polyethylene backing sheet, cannot be removed without either destroying the adhesive closure system or tearing the polyethylene sheet.

The present invention provides a pressure-sensitive adhesive closure which after being adhered to the polyethylene backing sheet of the diaper is easily removed, and repositioned, and again adhered to the polyethylene film. It has been found that particularly with respect to infant diapers in the toddler stage, it is desirable to be able to open the diaper to inspect it to see if the diaper needs changing. Previously available adhesive closure systems would either be destroyed or tear the polyethylene backing sheet upon opening, thus making the diaper useless. The adhesive closure of the present invention adheres to the polyethylene film thus securing the diaper in place about the wearer, but if it is desirable to open the diaper, the adhesive closure is easily removed for inspection, and then just as easily re-adhered to the polyethylene film, either in the same position, or in a different position.

SUMMARY OF THE INVENTION

According to the present invention, a disposable diaper is provided which has a pressure-sensitive adhesive closure, a moisture-permeable facing sheet, and a polyethylene or modified polyethylene moisture-impermeable backing sheet. The pressure-sensitive adhesive closure has a pressure-sensitive adhesive comprising a major proportion by weight of the total elastomers of an elastomeric and thermoplastic block polymer of the structure A-B-A, wherein A is a thermoplastic polymer block of a vinyl arene and possesses a glass transition temperature above normal room temperature and B is an elastomeric polymer block of isoprene, the thermoplastic A blocks composing about 8-35 percent by weight of the block polymer and about 25-125 parts by weight per 100 parts by weight of the total elastomers of a solid tackifier selected from the group consisting of rosin, rosin derivatives, polyterpenes, hydrocarbon resins, or mixtures thereof and preferably, from about 2 to about 25 parts by weight of lecithin per 100 parts by weight of the total elastomers. This adhesive composition provides a pressure-sensitive adhesive closure that may be reopened easily numerous times by separating the adhesive closure from the polyethylene backing sheet without substantial damage to the polyethylene backing sheet or to the adhesive closure.

The conventional adhesive tape tab fastener used on a disposable diaper, whether that diaper be appropriate for an adult or an infant, generally consists of a substrate which is coated on one side with adhesive. One end of the substrate or tape segment is coated with an adhesive which appropriately affixes the tape tab permanently to the outside surface of the diaper. Thus this end is identified as the fixed end. The other end of the adhesive tape segment is a free end. It is this free end which secures the diaper about the wearer when it is adhered to the outside diaper surface in an appropriate position.

When the adhesive tape tab fastener is in a storage position, the adhesive coated surface is in contact with a release means. The release means typically is a release strip carried on the outside surface of the diaper which is provided with a release-coated face.

Although the more conventional means of fastening a disposable diaper has been an adhesive tape tab fastener, the present invention includes not only an adhesive tape tab fastener but an adhesive closure wherein the adhesive composition used in this present invention is applied to the facing in the corners of the waist portion of the diaper at the back of the diaper. The diaper is provided with a suitable release surface for any area which may come into contact with the adhesive so that during manufacture and packing, the adhesive closure will not adhere to any part of the facing.

DETAILED DESCRIPTION OF THE INVENTION

Figure 1:
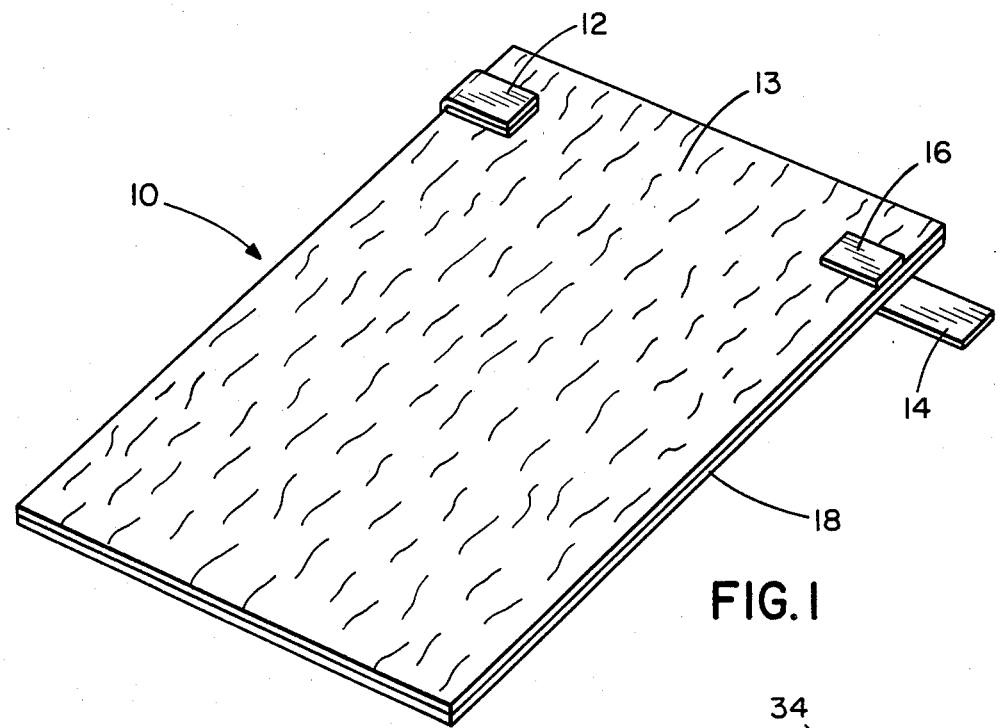
FIG. 1 is a perspective view of a diaper in accordance with one of the embodiments of the present invention.

FIG. 1 provides a perspective view of a disposable diaper 10 having a tape tab 12 in the storage position and a tape tab 14 in an opened, ready-to-use position. The tape tab 14 is affixed at the fixed end to the polyethylene backing sheet 18 in the storage position. The tape tab 14 is stored against release strip 16. The release strip 16 is adhered by adhesive to the facing sheet 13 of the diaper. The disposable diaper 10 is a typical disposable diaper having the moisture-impermeable polyethylene backing sheet 18, and the moisture-permeable facing sheet 13 with an absorbent batt sandwiched between the facing sheet and backing sheet.

Figure 2:
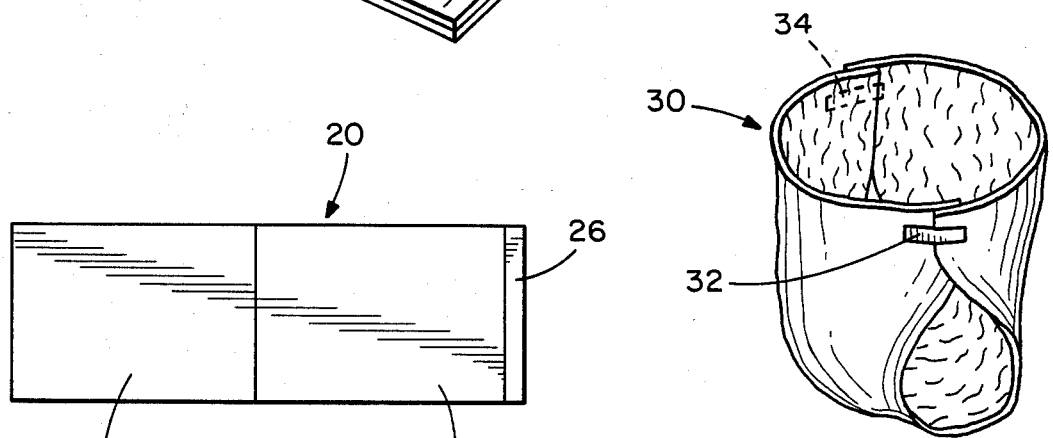
FIG. 2 is an enlarged plan view of a tab fastener used in an embodiment of the present invention.

FIG. 2 is a plan view of a typical adhesive tape tab fastener 20. The fastener has a fixed end 22 which is adhered to the backing sheet of a diaper by any suitable adhesive. The tab fastener also has a free end 24 to which the repositionable pressure-sensitive adhesive described above is applied. At the end of the free end 24 is a finger lift 26 which enables the user to easily open the tab fastener when it is in a storage position to ready it for use and to reopen the diaper when desired.

In use a diaper equipped with adhesive tape tab fasteners is applied to the wearer, which may be an infant or an adult, preferably by laying out the diaper on a suitable flat surface and placing the wearer thereon so that the waist-underlying end of the diaper is that having the tab fastener means. The other end of the diaper extends downwardly between the legs. Next the downwardly extending end of the diaper is brought up between the wearer's legs to a position contiguous with the front of the wearer's waist. The diaper is thereafter secured to the wearer by placing the corners of the waist portion of the abdomen-covering end as far around the wearer's waist as they will go, and by bringing the corners of the underlying end of the diaper into an overlapping relationship with the aforementioned corners so that the diaper snugly encircles the wearer's waist and provides a custom fit. The adhesive tape tab fasteners are then prepared for use by unfolding them to expose the adhesive coated face of the free end. The free end is extended to a working position. The tabs are then used to secure the diaper in the desired position by simply urging the pressure-sensitive adhesive surfaces in contact with the adjacent outer polyethylene surface of the diaper. The secured tape tab fasteners may be reopened for inspection of the diaper or repositioning for a more comfortable fit as many times as is desired.

Figure 3:
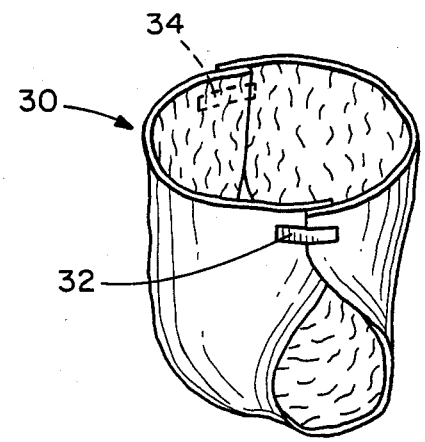
FIG. 3 is a perspective view of a diaper of the present invention in a configuration assumed by the diaper when placed about the wearer.
Figure 3A:
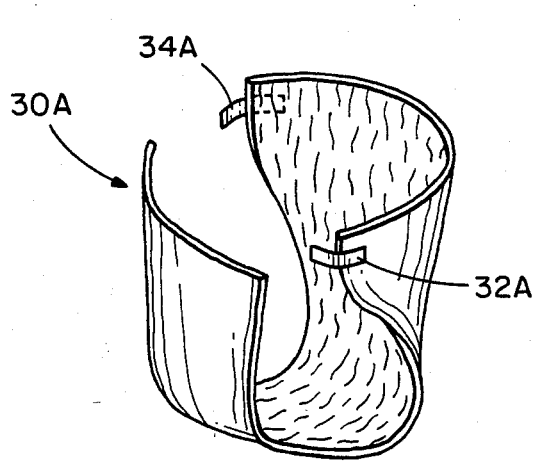
FIG. 3A is a perspective view of the diaper of FIG. 3 in a configuration when the diaper is opened for inspection.
Figure 3B:
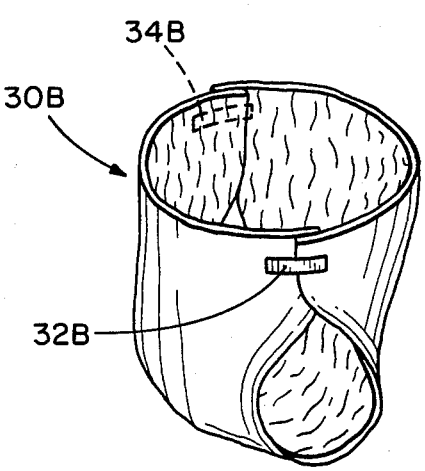
FIG. 3B is a perspective view of the diaper of FIGS. 3 and 3A in a configuration assumed when the diaper is reclosed.

FIGS. 3, 3A and 3B depict a diaper in a configuration assumed by the diaper when it is placed about a wearer. Specifically in FIG. 3 the diaper 30 has been secured about the waist of the wearer by tape tabs 32 and 34. In FIG. 3A the diaper 30A has been opened for inspection by opening the tab fasteners 32A and 34A. In FIG. 3B the diaper 30B has again been placed about the wearer by urging the pressure-sensitive adhesive surfaces of the free ends of tabs 32B and 34B in contact with the outer surface of the diaper where desired.

Adhesive tabs suitable for the purposes of the present invention can be made from a wide variety of materials provided that such materials are sufficiently flexible. For example, substrates such as cloth, saturated paper, film, foil and the like may be used as substrates for coating with adhesive. Each of the tape tab fasteners has a fixed end and a free end. Any adhesive composition which will affix the fixed end of the adhesive tape tab fastener to the polyethylene outside surface of the diaper is suitable for application to the fixed end of the tab. With respect to the free end or working end of the tape tab, the adhesive described above as a special adhesive is used so that once the diaper has been secured about the wearer the tape tab may easily be reopened either for inspection or repositioning the diaper in a more comfortable position.

The tape tab fastener preferably has a finger lift at the terminating end of the free working end. This permits opening the tab fastener whether it be in the storage position or in the secured position by grasping the finger lift end and pulling the tape tab away from the surface to which it is adhered.

The pressure-sensitive adhesive applied as a coating on the free end of the tape tab is an adhesive formulated with a major proportion by weight of the total elastomers of a specific type of block copolymer in combination with a specific type of tackifier and preferably a phosphatide including lecithin, cephalin and the like. The block polymer is both elastomeric and thermoplastic and has the structure A-B-A wherein A is a thermoplastic polymer block of a vinyl arene and possesses a glass transition temperature above normal room temperature and B is an elastomeric polymer block of isoprene or a copolymer therewith and the block polymer consists of about 8–35 percent by weight of A blocks. Preferably the A blocks have molecular weights of at least about 7,000. The block polymer structure A-B-A may be in a linear form, a radial form, or a simple form. The individual A blocks have a number average molecular weight of at least about 6,000 preferably in the range of about 8,000–30,000. The number average molecular weight of the B blocks for linear A-B-A block copolymers preferably is in the range of about 45,000–180,000 and that of the linear copolymer itself preferably is in the range of about 75,000–200,000. The number average molecular weight of the radial A-B-A block copolymers preferably is in the range of about 125,000–400,000. The simple block polymer, i.e. A-B, is used in minor amounts only, up to about 25 percent by weight, however the linear and radial copolymers may be used alone or in admixture with each other.

When the term "total elastomers" is used herein, it shall mean the aggregate block polymers. The tackifier used in combination with the elastomeric and thermoplastic block polymer is a resin or resin mixture which is solid at room temperature (about 25° C.) and is selected from rosin and rosin derivatives, polyterpene resins, and hydrocarbon resins. The amount of tackifier used is from about 25 to about 125 parts, preferably about 50–100 parts, per 100 parts of the total elastomers. The lecithin is preferably combined with the tackifier, the lecithin being present in an amount from about 2 to about 25 parts by weight per 100 parts of total elastomer.

Figure 4:
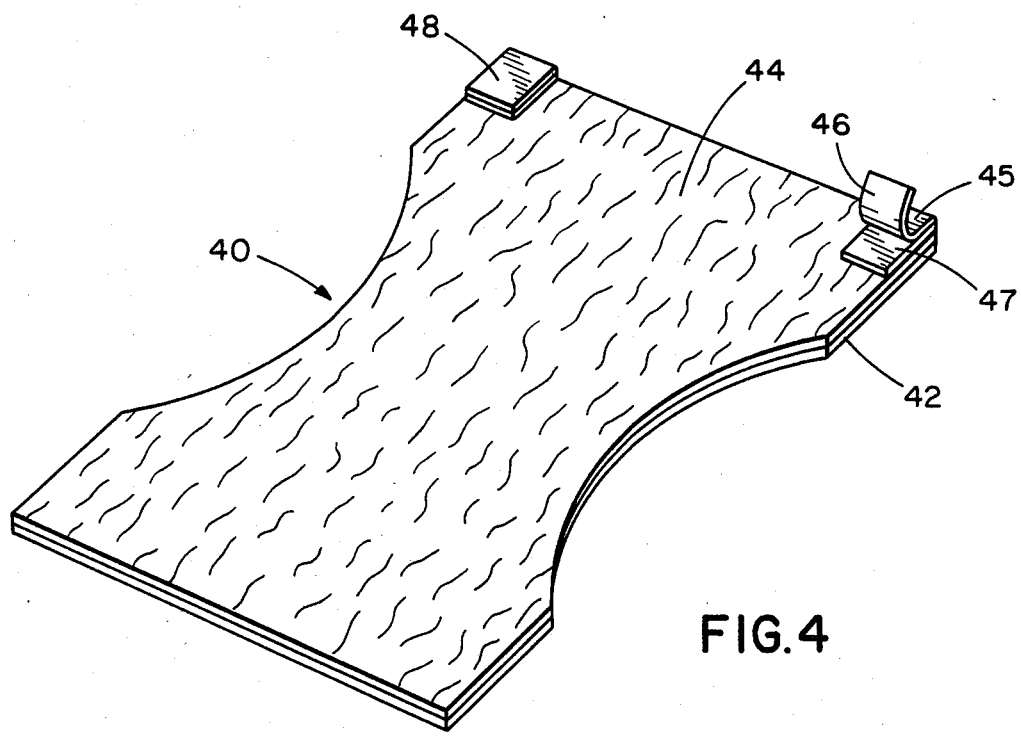
FIG. 4 is a perspective view of a diaper representing one embodiment of the present invention.

In another embodiment of the present invention depicted in FIG. 4 is a diaper 40 wherein the adhesive closures 45 and 48 are the special pressure-sensitive adhesive formulation applied in the corners of the facing 44 at the back waist portion of the diaper 40. For example, adhesive closure 45 consists of adhesive layer 47 covered by a removable release strip 46. When assuming a configuration about the wearer, the closures are adhered to the polyethylene backing 42.

Figures 5, 5A:
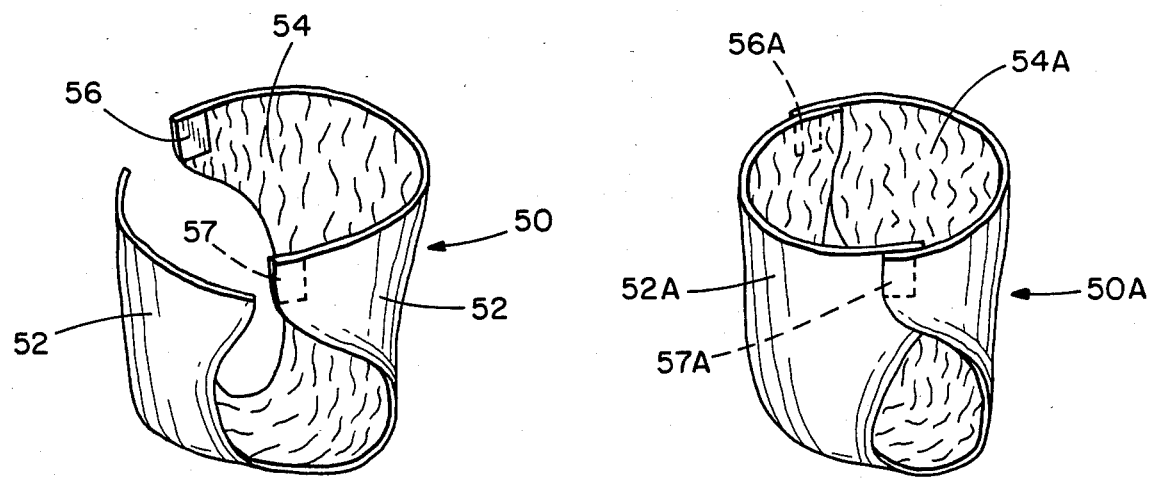
FIG. 5 is a perspective view of the diaper of FIG. 4 assuming a configuration as it is being placed on the wearer.
FIG. 5A is a perspective view of a diaper assuming the configuration after it has been placed on the wearer.

FIG. 5 depicts the diaper of FIG. 4 in a position about to be placed around the wearer. The diaper 50 contains adhesive closures 56 and 57 applied to the interior facing 54, their cover strips removed and ready for application to the polyethylene backing sheet 52. FIG. 5A depicts the diaper of FIG. 5 in its closed position. The diaper 50A has been secured about the wearer by pressing adhesive closures 56A and 57A onto the polyethylene backing 52A at the waist. The facing 54A contains no rough edges nor any exposed adhesive.

A typical diaper structure which may be used in the present invention consists of a moisture-permeable facing sheet, the polyethylene or modified polyethylene moisture-impermeable film as a backing sheet with an absorbent batt or panel sandwiched between the facing and the backing sheet. Generally the facing and backing sheets are larger in size than the absorbent panel so as to provide margin areas wherein the facing and backing may be adhered to each other to provide an integral unitary product. Heretofore it has not been possible to reopen a disposable diaper wherein the backing sheet is made of polyethylene or modified polyethylene films without either tearing the film or destroying the adhesive closure. The polyethylene or modified polyethylene films are suitable for disposable diaper production because of their relatively inexpensive costs and their moisture-impermeability preventing leakage of liquid from the diaper absorbent panel. However these films are not sufficiently strong to permit removing the typical adhesive closure, usually a tape tab, once it has been fastened. This means that the diaper cannot be opened for inspection or for repositioning to provide comfort, without rendering the diaper useless. Thus the present invention provides a diaper with a polyethylene film backing sheet and a pressure-sensitive adhesive closure which will reopen and permit inspection or repositioning of the adhesive closure.

The special adhesive used on the working portion of the adhesive closure that permits reopening from polyethylene also functions on substrates such as polypropylene, polyethylene terephthalate or the like which are relatively strong film backing sheets.

The following examples of suitable adhesive formulations for the special adhesive used in the adhesive closure of the present invention are given only by way of illustration and are not intended to limit the scope of the present invention in any way. In the examples, all proportions are given in parts per 100 parts of the total elastomers unless otherwise indicated. Adhesive substances suitable for the adhesive closure of the present invention are formulated by admixture as indicated in the following Table A:

TABLE A

| | EXAMPLE | | | | | |
|---|---|---|---|---|---|---|
| | 1 | 2 | 3 | 4 | 5 | 6 |
| Block Polymer Kraton 1107 | 100 | | | 100 | 100 | |
| Block Polymer Kraton 1111 | | 100 | 100 | | | |
| Block Polymer Solprene 420 | | | | | | 100 |
| Wingtack 95 Tackifier | | 80 | | | 80 | |
| Piccolyte S115 Tackifier | 75 | | | | | |
| Foral 105 Tackifier | | | | 80 | | |
| Escorez 5300 Tackifier | | | 80 | | | |
| Piccolyte S70 Tackifier | | | | | | 100 |
| Lecithin | 2.5 | 5 | 10 | | | |
| Antioxidants | 3 | 3 | 3 | 3 | 3 | 3 |

The adhesive formulations are coated on a suitable substrate such as a latex-saturated and release-coated paper, generally in an amount of about 1.5 ounces per square yard. The coating can be accomplished by solvent coating or extrusion coating or the like. When the adhesive is applied to the facing (FIGS. 4 and 5), transfer coating from a silicone liner to the facing fabric is the preferred method. The amount of adhesive is preferably above about 1.5 ounces per square yard of fabric.

Kraton 1107 is an elastomeric and thermoplastic styreneisoprene A-B-A block polymer sold by the Shell Chemical Company. The polymer is believed to have a styrene content of about 12–15 percent, a solution viscosity of 2900 cps, and a number average molecular weight of about 110,000–125,000. Whenever solution viscosity is mentioned in this application it refers to viscosity measured at 25° C. in a toluene solution at a solids content of about 25 percent.

Kraton 1111 is of similar structure to Kraton 1107 except the styrene content is 20–23 percent.

Solprene 420 is a radial styrene-isoprene-styrene block copolymer with a number average molecular weight of 240,000 and about 15 percent styrene.

Wingtack 95 is an unsaturated hydrocarbon resin believed to have been polymerized mainly from a mixture of piperylene and isoprene and which possesses a melting point of about 95° C. It is offered commercially by Goodyear Tire and Rubber Company.

Foral 105 tackifier is a pentaerythritol ester of a highly stabilized rosin having a melting point of 105° C. and is offered for sale by the Resins Division of Hercules Inc.

Escorez 5300 is a saturated hydrocarbon resin having a melting point of 100° C. It is offered for sale by Exxon Chemical Company.

Piccolyte S115 resin is a polyterpene resin of beta pinene having a melting point of 115° C. Piccolyte S70 is a similar polyterpene resin having a melting point of 70° C. Both products are offered for sale by Hercules Inc.

The antioxidants used in the formulation include Butyl zimate, and Santovar A and such typical antioxidants.

Each of the adhesive formulations in examples 1–6 are suitable for use in the adhesive closure of the present invention.

Having now described the invention in specific detail and exemplified the manner in which it may be carried into practice, it will be readily apparent to those skilled in the art that innumerable variations, applications, modifications, and extensions of the basic principles involved may be made without departing from its spirit or scope.

I claim:

1. In a disposable diaper having a pressure-sensitive adhesive closure, a moisture-permeable facing sheet, and a polyethylene or modified polyethylene moisture-impermeable backing sheet, the improvement which comprises the pressure-sensitive adhesive closure having a pressure-sensitive adhesive consisting essentially of at least about 44% by weight of the total elastomers of an elastomeric and thermoplastic block polymer of the structure A-B-A, wherein A is a thermoplastic polymer block of vinyl arene and possesses a glass transition temperature above normal room temperature and B is an elastomeric polymer block of isoprene, the thermoplastic A blocks composing about 8-35 percent by weight of the block polymer, and about 25-125 parts by weight of a tackifier solid at room temperature per 100 parts by weight of the total elastomers and 0-25 parts by weight of a phosphatide per 100 parts by weight of the total elastomers, said tackifier being selected from the group consisting of rosin, rosin derivatives, polyterpenes, hydrocarbon resins, or mixtures thereof, to provide a pressure-sensitive adhesive closure that may be reopened easily numerous times by separating the adhesive closure from the polyethylene backing sheet without substantial damage to the polyethylene backing sheet or to the adhesive closure.

2. A disposable diaper as in claim 1 wherein the pressure-sensitive adhesive closure is a tape tab fastener.

3. A disposable diaper as in claim 1 wherein the pressure-sensitive adhesive closure is a mass of adhesive applied to the facing at the corners of the waist portion at the back.

4. The disposable diaper of claim 1 wherein the A-B-A block polymer is an elastomeric and thermoplastic styrene-isoprene A-B-A block polymer.

5. The disposable diaper of claim 1 wherein the phosphatide is lecithin.

* * * * *